United States Patent [19]
Uno et al.

[11] Patent Number: 5,672,825
[45] Date of Patent: Sep. 30, 1997

[54] METHOD AND APPARATUS FOR DETECTING AND DISCRIMINATING OBJECTS UNDER THE GROUND

[75] Inventors: Masayoshi Uno; Tomonori Kimura; Masayoshi Kato, all of Kakamigahara, Japan

[73] Assignee: Kawasaki Jukogyo Kabushiki Kaisha, Kobe, Japan

[21] Appl. No.: 538,891

[22] Filed: Oct. 4, 1995

[30] Foreign Application Priority Data

Oct. 5, 1994 [JP] Japan .................. 6-264437

[51] Int. Cl.[6] ............................... G01N 29/12
[52] U.S. Cl. .................. 73/579; 73/602; 73/646
[58] Field of Search .................. 364/507, 508; 73/579, 597, 598, 602, 620, 646, 592

[56] References Cited

U.S. PATENT DOCUMENTS

| | | | |
|---|---|---|---|
| 3,600,937 | 8/1971 | Nilberg | 73/598 |
| 4,896,116 | 1/1990 | Nagashima et al. | 324/329 |
| 5,024,090 | 6/1991 | Pettigrew et al. | 73/572 |
| 5,357,063 | 10/1994 | House et al. | 367/14 |

*Primary Examiner*—Hezron E. Williams
*Assistant Examiner*—Rose M. Miller
*Attorney, Agent, or Firm*—Leydig, Voit & Mayer, Ltd.

[57] ABSTRACT

An elastic wave is applied to an object under the ground, so that an elastic wave which varies in accordance with the material and shape of the object under the ground is detected and the detected elastic wave is collated with characteristic data such as elastic wave data, or the like, of various objects registered in advance to thereby identify/discriminate the object under the ground. A vibration generating probe and a vibration receiving probe, or, alternatively, a vibration generating and receiving probe is put into the ground so as to come in contact with an object under the ground. Then, the vibration generating probe or vibration generating and receiving probe is hammered to generate an elastic wave. At least one of one longitudinal wave and two transverse waves of the elastic wave which has propagated to the object under the ground is received by the vibration receiving probe or vibration generating and receiving probe. The vibrations of the elastic wave are converted into an electrical signal by a vibration sensor, and frequency response characteristic (and/or time-response characteristic) of the elastic wave is detected by a signal processing portion or by a signal processing portion and a data processing portion. The characteristic data is compared/collated with elastic wave data of various objects under the ground collected in advance, so that an unknown object under the ground is identified/discriminated.

5 Claims, 5 Drawing Sheets

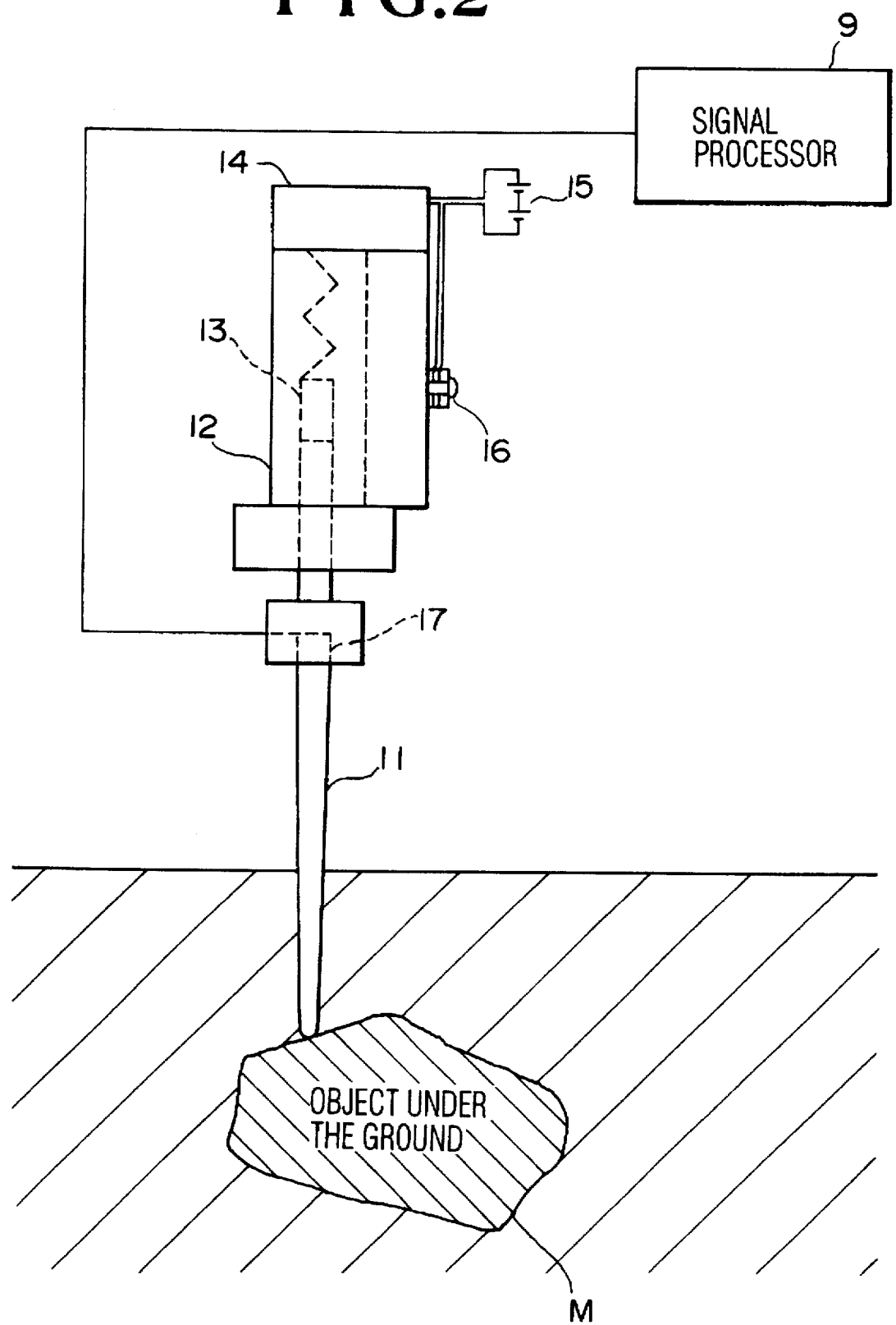

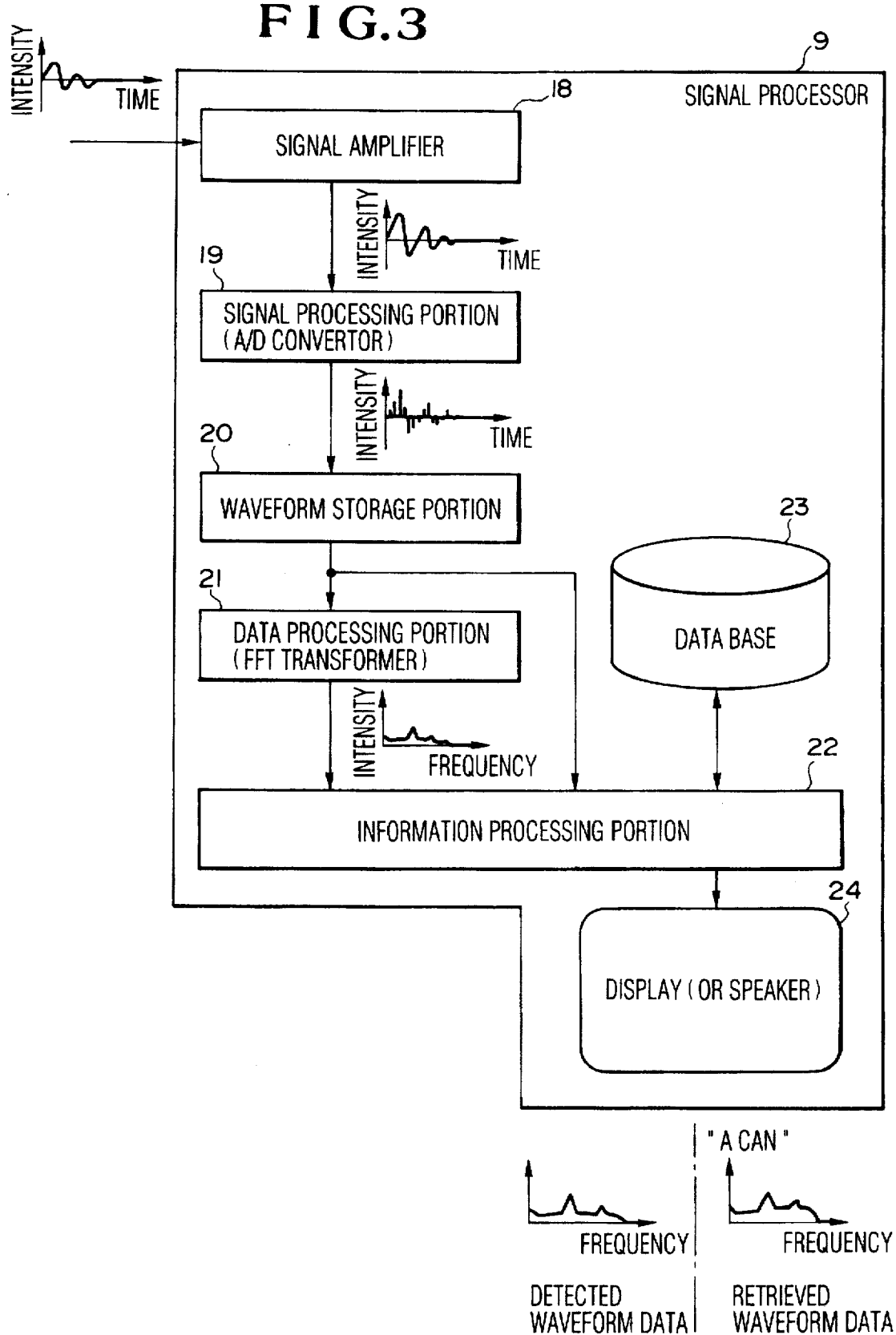

CAN

BRICK

METHOD AND APPARATUS FOR DETECTING AND DISCRIMINATING OBJECTS UNDER THE GROUND

BACKGROUND OF THE INVENTION

The present invention relates to a method and apparatus for detecting and discriminating objects under the ground remotely.

A conventional method of detecting objects under the ground uses magnetism, an electromagnetic wave, an ultrasonic wave, etc. Because the detecting method by using such means detects a reflected wave, a refracted wave, etc. from an object under the ground to thereby detect the object under the ground, information of the underground position and approximate size can be obtained, but information which enable to discriminate the object type (for example, the type of a bomb), the object material, etc. cannot be obtained (as the prior literatures of the technique of detecting general objects under the ground, there are JP-A-62-206480, JP-A-57-124268, JP-A-5-223923.)

For example, in a detecting method using an ultrasonic wave, a medium such as water, or the like, is required between an object under the ground and a sensor. Furthermore, in such a detecting method using an ultrasonic wave, there is a limitation that correct detection cannot be made unless an ultrasonic wave generating plane and a plane of an object under the ground are set to be parallel with each other. Accordingly, there arises a problem that detecting work is difficult. In addition, in a contact type detecting method using a portable probe, only the existence of objects under the ground can be obtained because the method attempts to detect the objects by the tactile sense of human hands or by the change of magnetism. Accordingly, there arises a problem that secure detection is difficult.

SUMMARY OF THE INVENTION

An object of the present invention is to provide a method and apparatus for detecting and discriminating objects under the ground to thereby make it possible to identify the shapes and materials of the objects under the ground.

The present invention is characterized in that elastic waves having frequency characteristics different from each other in accordance with the materials and shapes of objects under the ground are detected from the objects under the ground and collated with elastic wave characteristic data of various objects registered in advance.

To achieve the foregoing object, in a preferred method of detecting and discriminating objects under the ground according to the present invention, the respective ends of an elastic wave generating means and an elastic wave receiving means into contact with an object under the ground. Thereafter, an elastic wave is generated by the generating means and the elastic wave which has propagated to the object under the ground is received by the receiving means. The object under the ground is discriminated on the basis of vibration characteristic of the elastic wave.

In a more specific method of the detecting/discriminating method according to the present invention, a vibration generating probe and a vibration receiving probe are put into the ground and brought into contact with an object under the ground. Then, the vibration generating probe is hammered to generate an elastic wave and the elastic wave which has propagated to the object under the ground is received by the vibration receiving probe. The vibrations of the elastic wave are converted into an electrical signal by a vibration sensor and the electrical signal is transmitted to a signal processor. The time response of at least one of one longitudinal wave and two transverse waves of the elastic wave is detected by the signal processor. Further, function transformation is carried out to obtain frequency characteristic. Then, a result of comparison/collation of the frequency characteristic with data elastic waves of various objects under the ground collected in advance is displayed, or the object under the ground is discriminated by analytic estimate on the basis of the characteristic of the elastic wave, or an audible sound for identifying the object under the ground is generated on the basis of the characteristic of the elastic wave.

In a more specific method of the detecting/discriminating discriminating method according to the present invention, a vibration generating and receiving probe is put into the ground and brought into contact with an object under the ground. Then, the probe is hammered to generate an elastic wave and the elastic wave which has propagated to the object under the ground is received by the vibration generating and receiving probe. The vibrations of the elastic wave is converted into an electrical signal by a vibration sensor and the electrical signal is transmitted to a signal processor. In the signal processor, at least one of the frequency response characteristic and time-response characteristic of the elastic wave is detected. Then, a result of comparison/collation of the at least one of the frequency response characteristic and time-response characteristic of the elastic wave with data of elastic waves of various objects under the ground collected in advance is displayed, or the object under the ground is discriminated by analytic estimate on the basis of the characteristic of the elastic wave, or an audible sound for identifying the object under the ground is generated on the basis of the characteristic of the elastic wave.

To detect the time response of at least one of one longitudinal wave and two transverse waves of the elastic wave in the signal processor, first, the time-series electrical signal from the vibration sensor is amplified by a signal amplifier. Then, the analog signal is converted into a digital signal by an A/D converter, and the digital signal is held in a waveform storage portion. Then, the waveform data held in the waveform storage portion is subjected to function transformation by a function arithmetic operation portion to thereby obtain frequency response characteristic of the elastic wave. The frequency response characteristic is processed by a data processing portion and the result is displayed on a display. Or the processing portion may have a function of displaying the time-axis response waveform data held in the waveform storage portion on a display or a function of generating an audible sound by means of a separately provided sound source to identify the object under the ground.

A preferred apparatus for detecting and discriminating objects under the ground, according to the present invention, comprises: a vibration generating probe and a vibration receiving probe which are put into the ground so as to come into contact with an object under the ground; a hammer provided in a body of the vibration generating probe for generating an elastic wave in the vibration generating probe; a vibration sensor attached to the vibration receiving probe for picking up the vibrations of the elastic wave which has propagated from the vibration generating probe to the object under the ground and for converting the vibrations into an electrical signal; and a signal processor for processing the time-response electrical signal from the vibration sensor, for transforming the frequency response characteristic of the elastic wave, and for comparing/collating this with data of elastic waves of various objects collected in advance.

Another preferred apparatus for detecting and discriminating objects under the ground, comprises: a vibration generating and receiving probe which is put under the ground so as to be in contact with an object under the ground; a hammer provided in a body of the vibration generating and receiving probe for generating an elastic wave in the vibration generating and receiving probe; a vibration sensor attached to the vibration generating and receiving probe for picking up the vibrations of the elastic wave which has propagated from the vibration generating and receiving probe to the object under the ground and for converting the vibrations into an electrical signal; and a signal processor for detecting the frequency response characteristic and time-response characteristic of the elastic wave of the basis of the time-response electrical signal from the vibration sensor, and comparing/collating this with data of elastic waves of various objects collected in advance.

A preferred signal processor in the aforementioned two apparatuses of the present invention includes: a signal amplifier for amplifying the electrical signal obtained by the vibration sensor; an A/D converter for converting the analog signal from the signal amplifier into a digital signal; a waveform storage portion for holding the digital signal, as waveform data, from the A/D converter; an arithmetic operation portion for orthogonal-function-transforming the waveform data held in the waveform storage portion to thereby obtain frequency response characteristic of the elastic wave; an information processing portion for processing the frequency response characteristic data obtained by the arithmetic operation portion and the time-axis response waveform data held in the waveform storage portion; and a display (or an audible sound generating speaker or headphone) for searching the data processed by the information processing portion and the data of elastic waves of various objects under ground collected and registered in a data base in advance and for displaying results of processing.

In the method of detecting and discriminating objects under the ground according to the present invention, there is no limitation, unlike in the case of an ultrasonic detecting method, when the probe is brought into contact with an object under the ground, so that a characteristic elastic wave peculiar to the object under the ground can be detected regardless of mixing of foreign matters such as sand, soil, etc. into the contact surface, variations in the underground condition, variations in the impact force applied to the probe, and so on. Furthermore, an object under the ground can be identified/discriminated easily by comparing/collating the detected elastic wave with characteristic data such as elastic wave characteristic data, etc. of various objects under the ground registered in advance. For example, the type of an unexploded bomb under the ground can be discriminated. Furthermore, analytic prediction can be made on the basis of the characteristic of the elastic wave, and an audible sound identifying the object under the ground can be generated on the basis of the characteristic of the elastic wave characteristic.

In addition, by the apparatus for detecting and discriminating objects under the ground according to the present invention, the aforementioned detecting/discriminating method can be carried out accurately, securely and easily to improve the accuracy in detecting work, the reduction in time, and the safety in work.

BRIEF DESCRIPTION OF THE DRAWINGS

FIG. 2 is a diagram showing another embodiment of a detecting/discriminating apparatus for carrying out the method of detecting and discriminating objects under the ground according to the present invention;

FIG. 3 is a detailed diagram of a preferred embodiment of the signal processor in the detecting/discriminating apparatus depicted in FIGS. 1 and 2;

DESCRIPTION OF THE PREFERRED EMBODIMENTS

Figure 1:
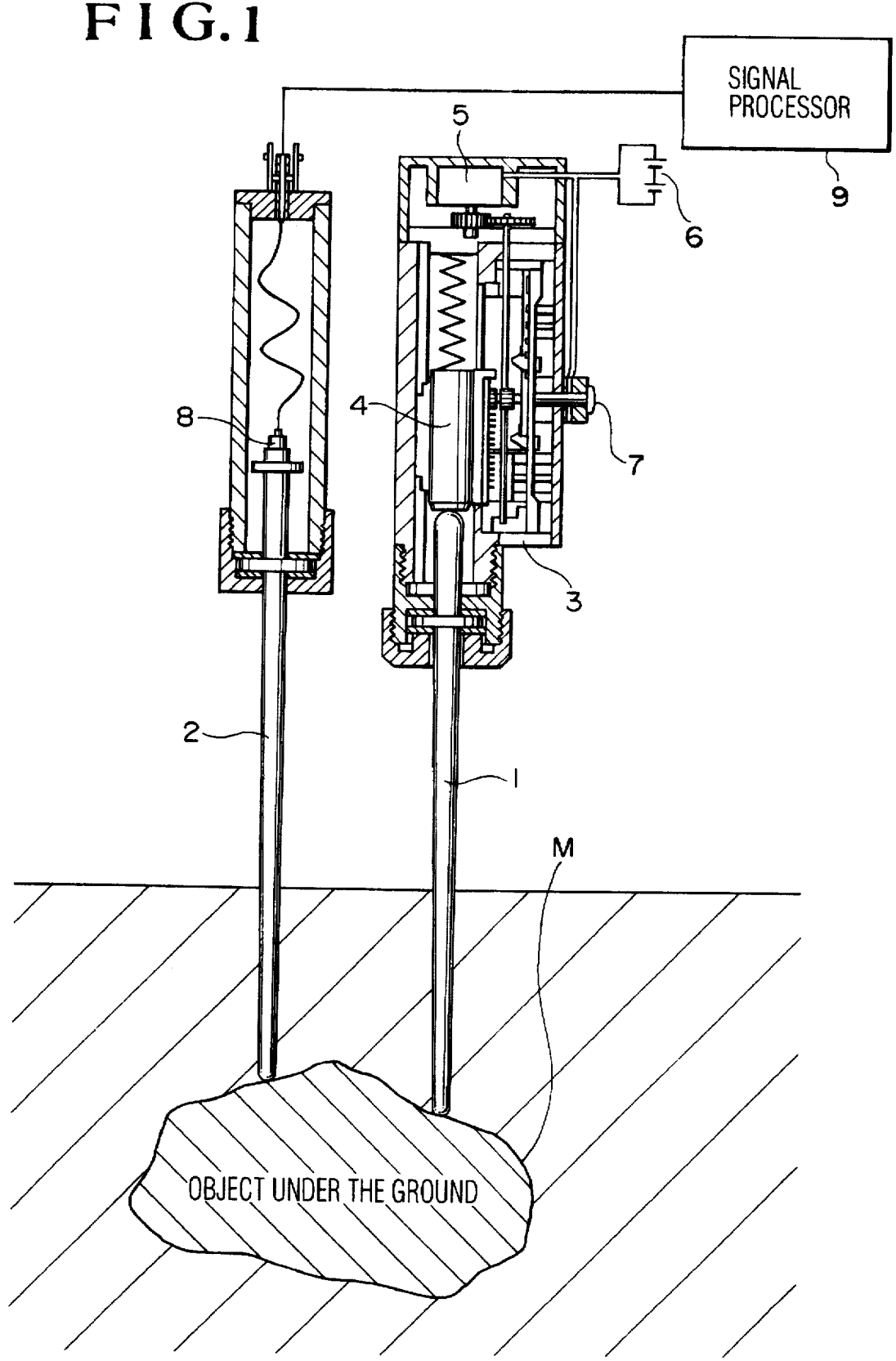
FIG. 1 is a diagram showing an embodiment of a detecting/discriminating apparatus for carrying out the method of detecting and discriminating objects under the ground according to the present invention.

Embodiments of the method and apparatus for detecting and discriminating objects under the ground according to the present invention will be described below. Referring now to FIG. 1, an embodiment of the detecting/discriminating apparatus is described.

In FIG. 1, numeral 1 designates a vibration generating probe which is put into the ground so as to come into contact with an object M under the ground; and 2, a vibration receiving probe which is put into the ground in the same manner as the vibration generating probe so as to come into contact with the object M under the ground. The vibration generating probe 1 is provided, in its body 3, with a hammer 4 for generating an elastic wave in the vibration generating probe 1, and a switch 7 for connecting an power supply 6 to a motor 5 for operating the hammer 4. The vibration receiving probe 2 is provided, at its upper end in its body 3, with a vibration sensor 8 for picking up vibrations of an elastic wave which has propagated from the vibration generating probe 1 to the object M under the ground and for converting the vibrations into an electrical signal. The vibration sensor 8 is connected to a signal processor 9 for detecting the time response of at least one of one longitudinal wave and two transverse waves of the elastic wave on the basis of the electrical signal supplied from the vibration sensor 8 and for comparing/collating the detected time response with elastic wave data of various objects under the Ground, which have been collected in advance.

Referring to FIG. 2, another embodiment of the detecting/discriminating apparatus according to the present invention will be described.

In FIG. 2, numeral 11 designates a vibration generating and receiving probe which is put into the ground so as to come into contact with an object M under the ground. The vibration generating and receiving probe 11 is provided, in its body 12, with a hammer 13 for generating an elastic wave in the vibration generating and receiving probe 11, and a switch 16 for connecting a power supply 15 to a motor 14 for operating the hammer 13. The vibration generating and receiving probe 11 is further provided with a vibration sensor 17 for picking up vibrations of an elastic wave propagated to the object M under the ground and for converting the vibrations into an electrical signal. The vibration sensor 17 is connected to a signal processor 9 for detecting the time response of at least one of one longitudinal wave and two transverse waves of the elastic wave on the basis of the electrical signal supplied from the vibration sensor 17 and for comparing/collating the detected time response with elastic wave data of various objects under the ground, which have been collected in advance.

Referring to FIG. 3, a preferred embodiment of the signal processor 9 in the two aforementioned embodiments of the detecting/discriminating apparatus will be described.

In FIG. 3, the signal processor 9 includes: a signal amplifier 18 for amplifying the electrical signal supplied from the vibration sensor 8 (or 17); an A/D converter 19 for converting an analog signal, which is the amplified electrical signal, supplied from the signal amplifier 18 into a digital signal; a waveform storage portion 20 for storing, as waveform data, the digital signal supplied from the A/D converter 19; an FFT arithmetic operation portion 21 for transforming the waveform data supplied from the waveform storage portion 20 into an orthogonal function (for example, Fourier transformation) to obtain frequency response characteristic of the elastic wave; an information processing portion 22 for processing the data of the frequency response characteristic obtained by the FFT arithmetic operation portion 21 and the data of the time-axis response waveform stored in the waveform storage portion 20; and a display (or an audible sound generating speaker or headphone) 24 for searching the data processed by the information processing portion 22 and the elastic wave data of various objects under the ground collected and registered in a data base 23 in advance and for displaying the retrieved data. Accordingly, the display (or speaker) 24 can be called an output means for outputting results of processing.

Incidentally, in the FFT arithmetic operation portion 21, other orthogonal function transformation such as wavelet transformation, or the like, may be used in place of the fast Fourier transformation (FFT).

An embodiment of the method of detecting and discriminating objects under the ground according to the present invention by using the detecting/discriminating apparatus shown in FIG. 1 will be described.

First, as shown in FIG. 1, the vibration generating probe 1 and the vibration receiving probe 2 are put into the ground so that the two probes 1 and 2 come into contact with an object M under the ground. Then, the switch 7 provided in the body 3 of the vibration generating probe 1 is pushed to connect the motor 5 to the power supply 6. The hammer 4 is driven by the motor 5 to vibrate to apply an impact load of from about 1N to about 3N to the vibration generating probe 1 so that an elastic wave is generated in the vibration generating probe 1. Then, the elastic wave which has propagated to the object M under the ground from the vibration generating probe 1 is received by the vibration receiving probe 2, so that the vibrations of the elastic wave is picked up by the vibration sensor 8 attached to the vibration receiving probe 2. The vibrations is converted into an electrical signal and the electrical signal is transmitted to the signal processor 9. In the signal processor 9, the frequency response characteristic of the elastic wave is detected by the FFT arithmetic operation portion constituted as a hardware structure and compared/collated with elastic wave data of various objects under the ground collected in advance. Thus, an unknown object under the ground is identified/discriminated.

Referring to FIG. 3, the signal processing operation of a preferred embodiment of the signal processor 9 will be described in detail.

In FIG. 3, first, the electrical signal from the vibration sensor 8 is amplified by the signal amplifier 18. Then, the amplified signal which is an analog signal is converted into a digital signal by the A/D converter 19. Then, the digital signal is stored as waveform data in the waveform storage portion 20. Then, the waveform data stored in the waveform storage portion 20 is Fourier-transformed by the FFT arithmetic operation portion 21 to obtain frequency response characteristic of the elastic wave. The thus obtained frequency response characteristic of the elastic wave and the time-axis response waveform data stored in the waveform storage portion 20 are processed by the information processing portion 22 and indicated on the display 24. On the other hand, elastic wave data of various objects under the ground collected and registered in the data base 23 in advance are searched and the retrieved data are displayed on the display 24 through the information processing portion 22. Alternatively, the detected elastic wave data is compared/collated with data in the data base 23 so that an unknown object under the ground is discriminated and the result of discrimination is displayed on the display 24. Alternatively, the information processing portion 22 compares/collates the detected elastic wave data with data in the data base 23 so that an unknown object under the ground is discriminated and an audible sound (for example, a voice informing the name of the object under the ground) expressing the result of discrimination is generated from the speaker 24. When, for example, the object under the ground is a can, the speaker 24 announces "CAN".

Another embodiment of the method of detecting and discriminating objects under the ground according to the present invention by using the detecting/discriminating apparatus shown in FIG. 2 will be described.

In FIG. 2, first, the vibration generating and receiving probe 11 is put into the ground so that the probe 11 is brought into contact with an object M under the ground. Then, the switch 13 provided in the body 12 of the vibration generating and receiving probe 11 is pushed to connect the motor 14 to the electrical source 15. The hammer 13 is driven by the motor 14 to vibrate to apply an impact load of from about 1N to about 3N to the vibrating generating and receiving probe 11 to thereby generate an elastic wave in the probe 11. Then, the elastic wave which has propagated to the object M under the ground is received by the vibration generating and receiving probe 11, so that the vibrations of the elastic wave is picked up by the vibration sensor 17 attached to the vibration generating and receiving probe 11. The vibrations are converted into an electrical signal and transmitted to the signal processor 9. In the signal processor 9, signal processing is carried out in the same manner as in the previous embodiment so that an unknown object M under the ground is identified/discriminated. Because there is a time lag (for example, at least about 1/1000 sec. in the case where the length of the probe 11 is 10 cm) between the elastic wave generated by the vibration of the hammer 13 and the elastic wave which has propagated to the object M under the ground, only the elastic wave propagated to the object under the ground can be extracted easily by performing suitable signal masking in the signal processor 9.

Although the vibration generating and receiving probe 11 shown in FIG. 2 is an integrated type probe, a coaxial type probe provided by slidably fitting a vibration generating probe into a tubular vibration receiving probe may be used as the vibration generating and receiving probe 11.

FIGS. 4A and 4B and FIGS. 5A and 5B show the relation between an object under the ground and frequency response characteristic.

Figure 4A:
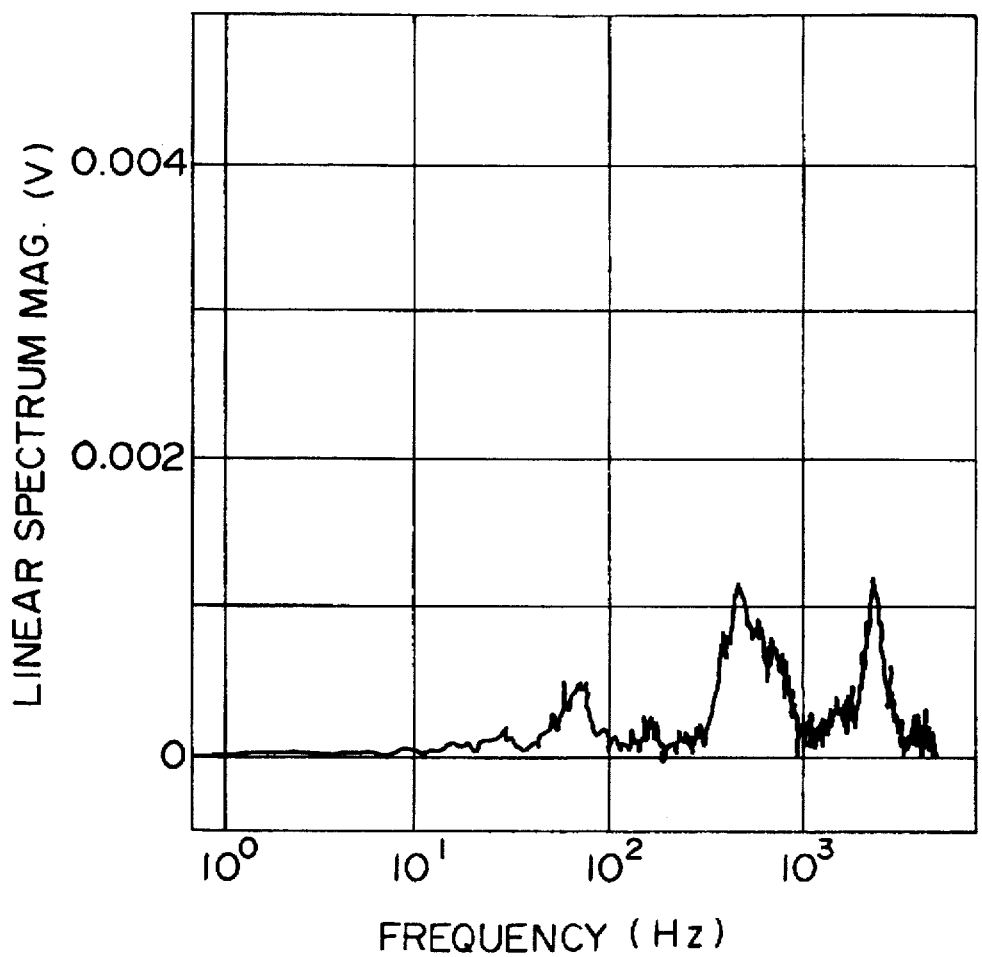
FIGS. 4A and 4B are a graph and a view showing an example of the relation between an object under the ground and a waveform.
Figure 4B:
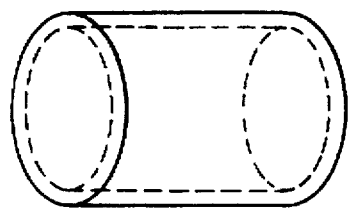
Figure 5A:
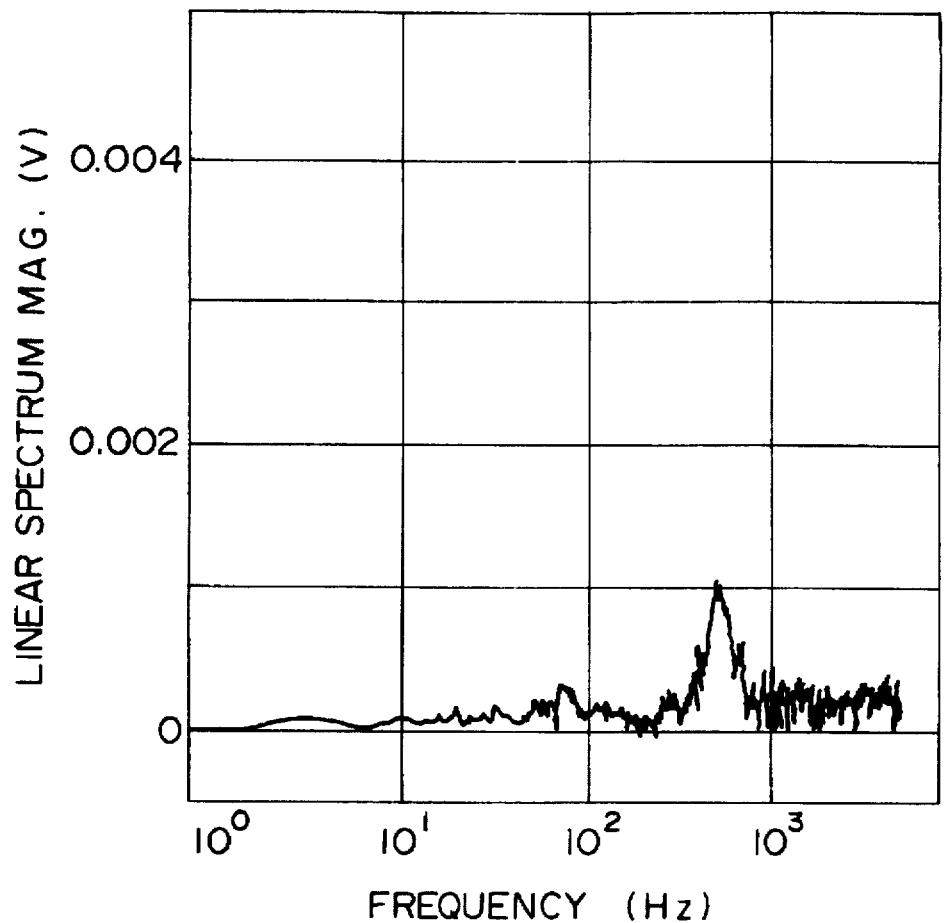
FIGS. 5A and 5B are a graph and a view showing another example of the relation between an object under the ground and a waveform.
Figure 5B:
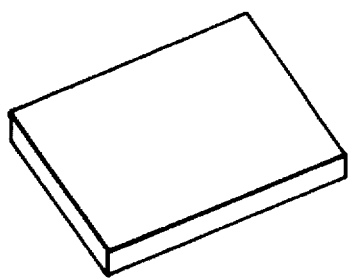

FIG. 4A shows frequency response characteristic in the case where a can as shown in FIG. 4B is laid under the ground. FIG. 5A shows frequency response characteristic in the case where a brick as shown in FIG. 5B is laid under the ground. In this manner, objects under the ground can be discriminated by the difference in frequency response characteristic.

We claim:

1. A method of detecting and discriminating objects under the ground, comprising the steps of:
   bringing an end of a single vibration generating and receiving probe into contact with an object under the ground;
   generating an elastic wave in the probe;
   reflecting the elastic wave off of the object;
   receiving the reflected elastic wave which has propagated through the single probe to the object under the ground; and
   discriminating the object under the ground on the basis of a vibration characteristic of the reflected elastic wave.

2. A method of detecting and discriminating objects under the ground, comprising the steps of:
   putting a vibration generating and receiving probe into the ground to bring said probe into contact with an object under the ground;
   hammering said probe to generate an elastic wave;
   receiving, by said vibration generating and receiving probe, the elastic wave which has propagated to the object under the ground;
   converting, by a vibration sensor, vibrations of the elastic wave into an electrical signal and transmitting the electrical signal to a signal processor;
   detecting, by a data processor, frequency response characteristic; and
   executing either one of an operation of displaying results of comparison/collation of the frequency response characteristic with data of elastic waves of various objects under the ground collected in advance and another operation of generating an audible sound for discriminating the object under the ground.

3. A method of detecting and discriminating objects under the ground according to claim 2,
   wherein time response of either one of one longitudinal wave and two transverse waves of the elastic wave is detected by said signal processor before step of detecting the frequency response characteristic, and
   wherein the frequency response characteristic detecting step includes the steps of:
   amplifying, by a signal amplifier, the time-response electrical signal from said vibration sensor;
   converting, by an A/D converter, the analog signal into a digital signal;
   holding the digital signal in a waveform storage portion;
   orthogonal-function-transforming, by a data processing portion, the waveform data held in said waveform storage portion to thereby obtain frequency response characteristic of the elastic wave; and
   processing, by an information processing portion, the frequency response characteristic and supplying results of processing to an output means.

4. An apparatus for detecting and discriminating objects under the ground, comprising:
   a vibration generating and receiving probe which is put into the ground so as to come into contact with an object under the ground;
   a hammer provided in a body of said vibration generating and receiving probe for generating an elastic wave in said vibration generating and receiving probe;
   a vibration sensor attached to said vibration generating and receiving probe for picking up vibrations of the elastic wave which has propagated from said vibration generating and receiving probe to the object under the ground and for converting the vibrations into an electrical signal; and
   a signal processor for detecting time response of at least one of one longitudinal wave and two transverse waves of the elastic wave on the basis of the time-series electrical signal from said vibration sensor and for comparing/collating the time response with data of elastic waves of various objects collected in advance.

5. An apparatus for detecting and discriminating objects under the ground according to claim 4, wherein said signal processor includes:
   a signal amplifier for amplifying the electrical signal from said vibration sensor;
   a signal processing portion for converting the analog signal from said signal amplifier into a digital signal;
   a waveform storage portion for holding the digital signal, as waveform data, from said signal processing portion;
   a data processing portion for orthogonal-function-transforming the waveform data from said waveform storage portion to thereby obtain frequency response characteristic of the elastic wave;
   an information processing portion for processing data of the frequency response characteristic obtained by said data processing portion and data of time-axis response waveforms held in said waveform storage portion; and
   an output means for searching data supplied to said information processing portion and data of elastic waves of various objects under ground collected and registered in a data base in advance and for outputting results of processing.

* * * * *